US010646110B2

(12) United States Patent
Fukuda

(10) Patent No.: US 10,646,110 B2
(45) Date of Patent: May 12, 2020

(54) ENDOSCOPE SYSTEM THAT DISPLAYS TWO STILL IMAGES OF A SUBJECT ILLUMINATED BY TWO TYPES OF LIGHTS HAVING DIFFERENT WAVELENGTH BANDS

(71) Applicant: HOYA CORPORATION, Tokyo (JP)

(72) Inventor: Masaaki Fukuda, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 491 days.

(21) Appl. No.: 15/513,618

(22) PCT Filed: Oct. 12, 2016

(86) PCT No.: PCT/JP2016/080232
§ 371 (c)(1),
(2) Date: Mar. 23, 2017

(87) PCT Pub. No.: WO2017/069024
PCT Pub. Date: Apr. 27, 2017

(65) Prior Publication Data
US 2017/0290496 A1    Oct. 12, 2017

(30) Foreign Application Priority Data
Oct. 23, 2015  (JP) ................................ 2015-209068

(51) Int. Cl.
*A61B 1/06* (2006.01)
*A61B 1/045* (2006.01)
(Continued)

(52) U.S. Cl.
CPC .............. *A61B 1/05* (2013.01); *A61B 1/0005* (2013.01); *A61B 1/00009* (2013.01);
(Continued)

(58) Field of Classification Search
CPC . A61B 1/00009; A61B 1/0638; A61B 1/0646; A61B 1/0669; A61B 1/04;
(Continued)

(56) References Cited

U.S. PATENT DOCUMENTS 4,901,143 A * 2/1990 Uehara ..................... A61B 1/05
348/220.1
5,164,824 A * 11/1992 Ieoka .................. H04N 5/2353
348/231.99
(Continued)

FOREIGN PATENT DOCUMENTS

JP            5-30460        2/1993
JP          10323326 A *   12/1998
(Continued)

OTHER PUBLICATIONS

International Search Report and Written Opinion (ISR/WO) in International Patent Application No. PCT/JP2016/080232, dated Dec. 6, 2016, together with an English language translation of ISR.

Primary Examiner — John P Leubecker
(74) Attorney, Agent, or Firm — Greenblum & Berstein, P.L.C.

(57) ABSTRACT

An endoscope system includes: a light source unit that alternatingly emits first illumination light and second illumination light; an imaging means for generating a first image signal of a subject illuminated by the first illumination light, and generating a second image signal of the subject illuminated by the second illumination light; a first image signal storing means for storing the first image signals; a second image signal storing means for storing the second image signals; an image evaluation value calculating means for calculating at least one of image evaluation values based on the first image signals and image evaluation values based on the second image signals; an image signal selecting means for selecting a first display image signal and selecting
(Continued)

a second display image signal based on the image evaluation values; and a displaying means for displaying a first image and a second image that are based on the first display image signal and the second display image signal respectively.

5 Claims, 5 Drawing Sheets

(51) Int. Cl.
*A61B 1/05* (2006.01)
*G02B 23/24* (2006.01)
*A61B 1/00* (2006.01)
*A61B 5/00* (2006.01)

(52) U.S. Cl.
CPC .......... *A61B 1/0638* (2013.01); *A61B 1/0646* (2013.01); *A61B 1/0676* (2013.01); *G02B 23/2453* (2013.01); *G02B 23/2469* (2013.01); *A61B 1/045* (2013.01); *A61B 5/0084* (2013.01); *A61B 5/6873* (2013.01)

(58) Field of Classification Search
CPC ..... A61B 1/0005; A61B 1/045; A61B 1/0002; A61B 5/0084; H04N 5/23264; H04N 5/23267; H04N 2005/2255; G06T 5/003
See application file for complete search history.

(56) References Cited

U.S. PATENT DOCUMENTS

| | | | | |
|---|---|---|---|---|
| 5,617,136 A * | 4/1997 | Iso | .......... | H04N 1/00 348/65 |
| 8,548,235 B2 * | 10/2013 | Suzuki | ............. | H04N 5/23264 382/167 |
| 2002/0021355 A1 * | 2/2002 | Utsui | .............. | A61B 1/0638 348/65 |
| 2005/0078175 A1 * | 4/2005 | Kaneko | ............. | A61B 1/00009 348/65 |
| 2006/0256191 A1 * | 11/2006 | Iketani | ............... | A61B 1/0005 348/65 |
| 2007/0013771 A1 * | 1/2007 | Imaizumi | ........... | A61B 1/00009 348/74 |
| 2010/0063352 A1 * | 3/2010 | Matsuura | ............. | A61B 1/0638 600/103 |
| 2010/0063355 A1 * | 3/2010 | Matsuura | ............... | A61B 1/045 600/109 |
| 2012/0086790 A1 * | 4/2012 | Takahira | ........... | A61B 1/00048 348/68 |
| 2013/0158352 A1 * | 6/2013 | Imaizumi | ........... | A61B 1/00009 600/111 |
| 2015/0182106 A1 * | 7/2015 | King | ..................... | A61B 1/043 600/431 |
| 2016/0128545 A1 * | 5/2016 | Morita | ................ | A61B 1/0002 600/109 |
| 2016/0156822 A1 * | 6/2016 | Iwasaki | ............. | G02B 23/2461 348/68 |
| 2019/0052854 A1 * | 2/2019 | Kojima | ................. | G02B 23/24 |

FOREIGN PATENT DOCUMENTS

| | | |
|---|---|---|
| JP | 3887453 | 2/2007 |
| JP | 2012-239757 | 12/2012 |
| JP | 2014-220690 | 11/2014 |

* cited by examiner

ENDOSCOPE SYSTEM THAT DISPLAYS TWO STILL IMAGES OF A SUBJECT ILLUMINATED BY TWO TYPES OF LIGHTS HAVING DIFFERENT WAVELENGTH BANDS

TECHNICAL FIELD

The present invention relates to an endoscope system for performing pause (freeze) processing on a moving image that has been captured.

BACKGROUND ART

An endoscope system that includes an endoscope unit, a processor unit, and a monitor is known as an endoscope system for observing a subject in a body cavity such as a person's esophagus or intestine. Illumination light emitted from the processor unit is guided in a light guide fiber bundle provided in the endoscope unit and emitted from a light distribution window provided at the distal end of the endoscope unit. The illumination light emitted from the light distribution window is reflected by a subject in the body cavity and is received as object light through an observation window provided at the distal end of the endoscope unit. The object light received through the observation window is converted into an electrical signal at a predetermined frame rate by an image sensor, and the electrical signal is output to the processor unit. The processor unit includes a signal processing circuit, and the received electrical signal is converted into an image signal by the signal processing circuit and transmitted to the monitor. The monitor displays a moving image based on the image signal received from the processor unit. Accordingly a user (operator) who is using the endoscope system is able to observe the subject by viewing the moving image displayed on the monitor. Also, if a freeze instruction for pausing (freezing) the moving image is input to the processor unit by the operator, a still image of the subject is displayed on the monitor. This allows the operator to inspect the subject. However, depending on the timing at which the operator inputs the freeze instruction, there have been cases where the still image displayed on the monitor is motion-blurred or defocused.

An endoscope system that is related to the aforementioned issue and suppresses color shift in a still image is disclosed in Japanese Patent No. 3887453 (referred to hereinafter as "Patent Document 1"). In the light source apparatus for an endoscope disclosed in Patent Document 1, a frame image in which color shift is lower than a predetermined value is selected from a moving image displayed at a predetermined frame rate, and is stored as a still image. Here, the number of still images that can be stored is limited, and the still images are updated in order of oldest image. In this endoscope system, when a freeze instruction is input, the still image of the frame that has the least amount of color shift is selected from among the stored still images, and is displayed. Accordingly, when a freeze instruction is input, a still image having little color shift is displayed on the monitor.

SUMMARY OF INVENTION

An endoscope system is known in which two types of illumination light having different wavelength bands are alternatingly emitted at a predetermined frame rate, and images of the subject illuminated by the two types of illumination light are generated and displayed on the same screen of a monitor at the same time. Consider the case where the processing method disclosed in Patent Document 1 is applied to this type of endoscope system. In this case, the manner in which motion-blur and defocus occur in a still image changes according to the brightness and wavelength band of the illumination light that illuminates the subject, and therefore the extent of motion-blur and defocus that occurs is different between the two types of subject images that correspond to the two types of illumination light that have different wavelength bands. For this reason, it is difficult to select a frame that is suited to display as a still image, and there is a risk of motion-blur and defocus occurring in both of the two types of subject images.

The present invention was achieved in light of the above-described circumstances, and an object thereof is to provide an endoscope system that is for displaying images of a subject illuminated by two types of illumination light that have different wavelength bands, and that is advantageous to displaying a still image in which motion-blur and defocus are suppressed.

In order to achieve the above-described object, an endoscope system according to an embodiment of the present invention includes: a light source unit that alternatingly emits first illumination light and second illumination light at a predetermined cycle, the first illumination light and the second illumination light having mutually different wavelength bands; an imaging means for imaging a subject illuminated by the first illumination light and generating a first image signal, and imaging the subject illuminated by the second illumination light and generating a second image signal; a first image signal storing means for successively storing generated first image signals; a second image signal storing means for successively storing generated second image signals; an image evaluation value calculating means for calculating at least one of image evaluation values of first images that are based on the stored first image signals and image evaluation values of second images that are based on the stored second image signals; an image signal selecting means for selecting a first display image signal from among a plurality of the stored first image signals, and selecting a second display image signal from among a plurality of the stored second image signals, based on the calculated image evaluation values; and a displaying means for displaying a first image that is based on the first display image signal and a second image that is based on the second display image signal at the same time.

According to this configuration, the first display image signal and the second display image signal are independently selected based on at least one of the result of image evaluation of the first images and the result of image evaluation of the second images. Accordingly, an image signal that is suited to the display of a still image is selected for at least one of the first display image signal and the second display image signal.

Also, the endoscope system may further include an instruction receiving means for receiving a freeze instruction from a user. In this case, the image evaluation value calculating means weights each of the calculated image evaluation values according to a time difference between a time when an image corresponding to the image evaluation value was captured and a time when the instruction receiving means received the freeze instruction.

Also, the image evaluation value calculating means may perform the weighting by adding an addend to the image evaluation value or multiplying the image evaluation value by a multiplier, the addend or the multiplier being higher the smaller the time difference is.

Also, the image signal selecting means may select the first display image signal from among a plurality of the stored first image signals based on the image evaluation values, and select, as the second display image signal, the second image signal of the same frame as a frame of the first display image signal, or the second image signal of a frame that is a predetermined number of frames before or a predetermined number of frames after the frame of the first display image signal.

Also, in a case where a new first image signal is generated by the imaging means when a predetermined number of first image signals are stored, the first image signal storing means may store the newly generated first image signal by overwriting a first image signal that has an oldest storage time among the stored first image signals, and in a case where a new second image signal is generated by the imaging means when a predetermined number of second image signals are stored, the second image signal storing means may store the newly generated second image signal by overwriting a second image signal that has an oldest storage time among the stored second image signals.

According to the present invention, an endoscope system that is for displaying an image of a subject illuminated by two types of illumination light that have different wavelength bands, and that is advantageous to displaying a still image in which motion-blur and defocus are suppressed is provided.

DESCRIPTION OF EMBODIMENTS

Hereinafter, an embodiment of the present invention will be described with reference to the drawings.

Figure 1:
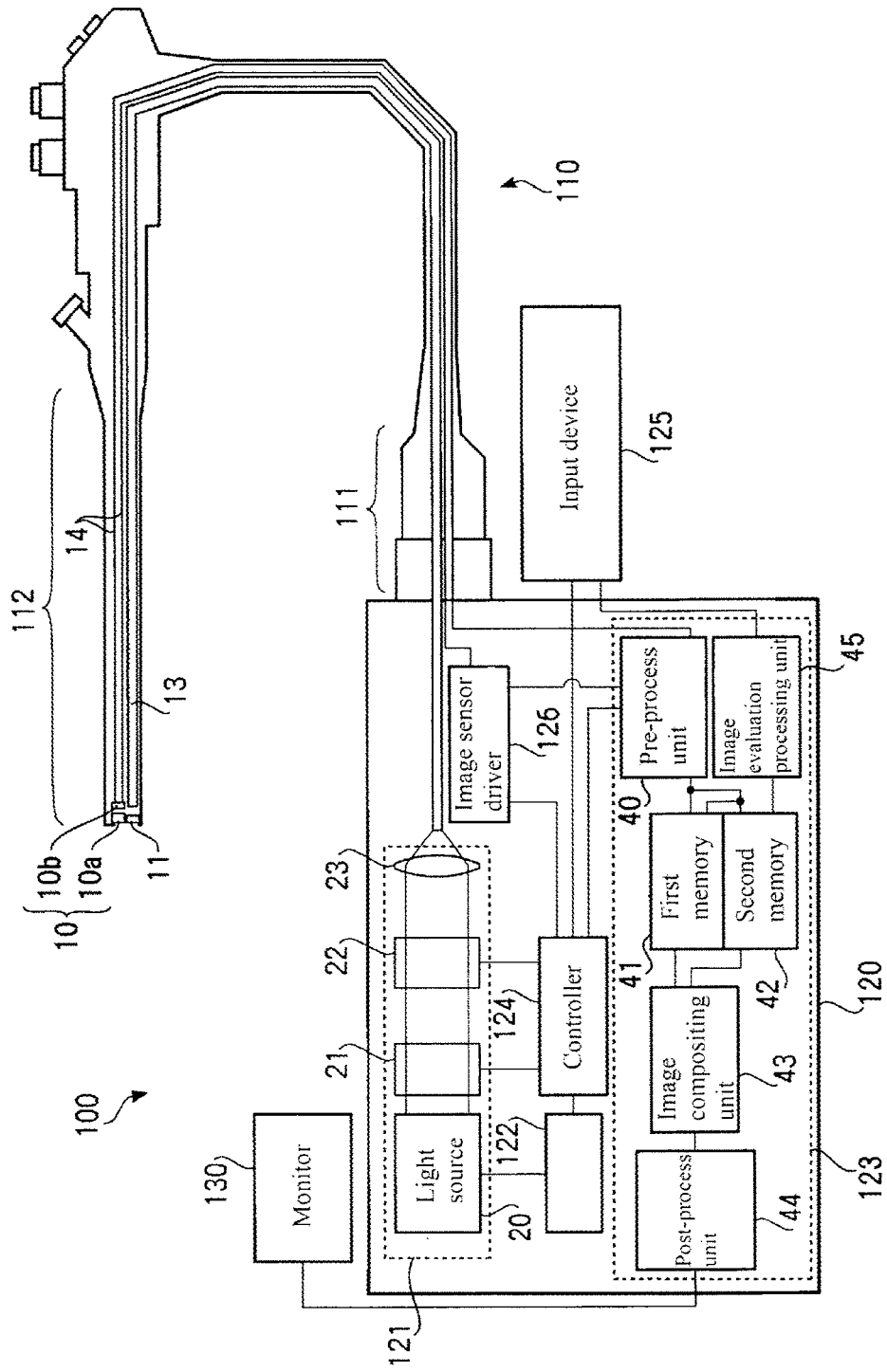
FIG. 1 is a block diagram of an endoscope system according to an embodiment of the present invention.

FIG. 1 is a block diagram showing the configuration of an endoscope system 100 according to an embodiment of the present invention. The endoscope system 100 of the present embodiment is a medical imaging system that is used in order to observe a subject in a person's body cavity. As shown in FIG. 1, the endoscope system 100 includes an endoscope unit 110, a processor unit 120, and a monitor 130.

The endoscope unit 110 has a connector portion 111 and an insertion tube 112. An imaging unit 10 and a light distribution lens 11 that function as an imaging means are provided in the distal end portion of the insertion tube 112. Also, a light guide fiber bundle 13 and multiple wires 14 are provided extending from the connector portion 111 to the distal end portion in the endoscope unit 110.

The processor unit 120 includes a light source unit 121, a light source drive circuit 122, an image processing unit 123, a controller 124, an input device 125, and an image sensor driver 126.

Figure 2:
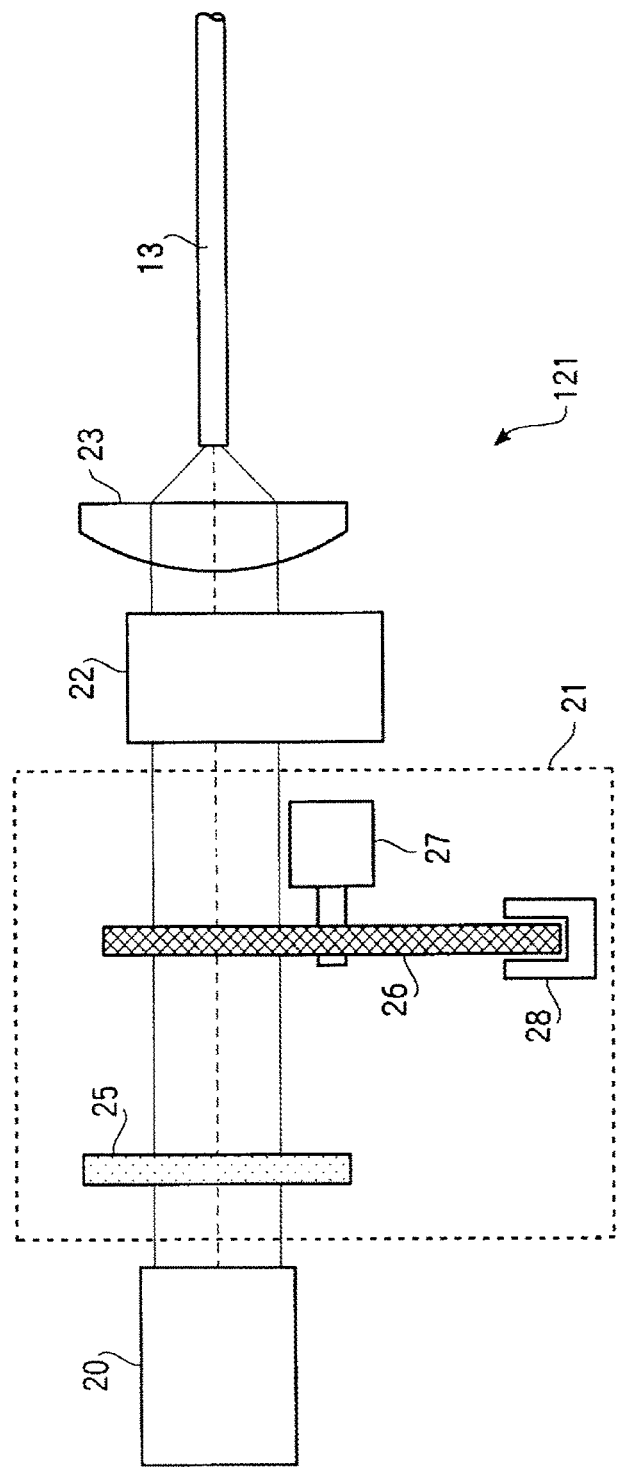
FIG. 2 is a block diagram of a light source unit according to the embodiment of the present invention.

FIG. 2 is a block diagram of the light source unit 121. The light source unit 121 includes a light source 20, a filter unit 21, a light adjustment unit 22, and a condensing lens 23. The light source 20 is driven by the light source drive circuit 122 and emits white illumination light. The illumination light emitted from the light source 20 enters the filter unit 21. The filter unit 21 has an IR (infrared) cut filter 25 and a filter turret 26. The illumination light that enters the filter unit 21 passes through the IR cut filter 25 and the filter turret 26 in the stated order, and then enters the light adjustment unit 22.

Figure 3:
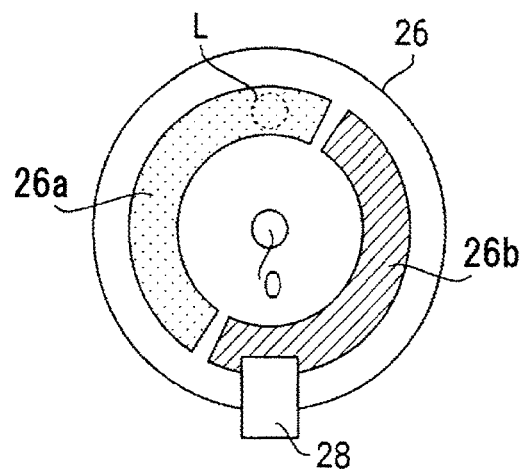
FIG. 3 is a front view of a filter turret according to the embodiment of the present invention.

FIG. 3 is a front view in which the filter turret 26 is viewed from the light source 20 side. The filter turret 26 is shaped as a circular disk. As shown in FIG. 3, the filter turret 26 has a first optical filter 26a and a second optical filter 26b that have different spectral characteristics and are arranged side-by-side in the circumferential direction. These optical filters are shaped as fans that spread out in an angular range (here, an angular range of approximately 180°) that corresponds to a predetermined field rate (1/60 seconds in the present embodiment).

Figure 4:
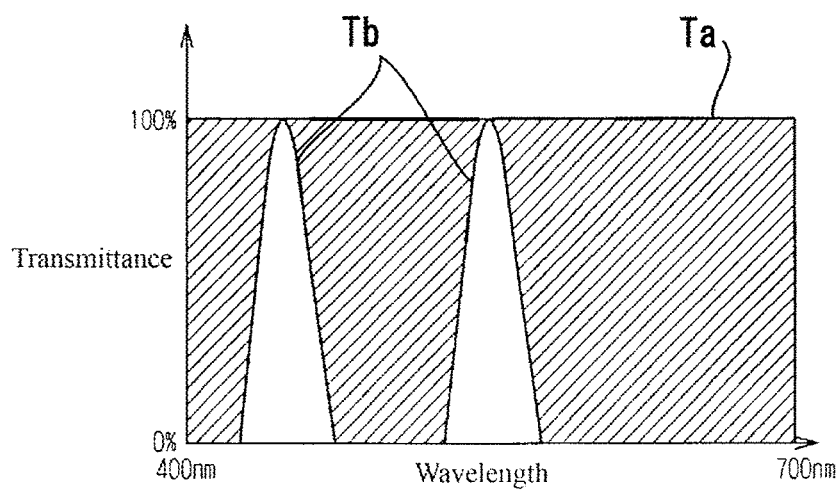
FIG. 4 is a diagram showing spectral characteristics of optical filters according to the embodiment of the present invention.

The filter turret 26 is rotated by a motor 27 and extracts, from white illumination light emitted from the light source 20 (see a region L shown by a dashed line in FIG. 3), one of two types of illumination light that have different spectrums at a timing synchronized with imaging performed by the later-described imaging unit 10. Here, FIG. 4 shows the spectral characteristics of the first optical filter 26a and the second optical filter 26b. In FIG. 4, the horizontal axis indicates the wavelength (unit: nm), and the vertical axis indicates the transmittance (unit: %). As shown in FIG. 4, a transmittance Ta of the first optical filter 26a is approximately 100% with respect to light in the visible wavelength band of approximately 400 nm to approximately 700 nm. For this reason, the illumination light that passes through the first optical filter 26a is white light. On the other hand, the second optical filter 26b has a high transmittance Tb with respect to light with a wavelength around 450 nm (blue light) and light with a wavelength around 550 nm (green light), and has a low transmittance Tb with respect to light of other wavelengths. For this reason, the illumination light that passes through the second optical filter 26b is blue light and green light that mix to make the color cyan. Hereinafter, for the sake of convenience in the description, the illumination light that passes through the first optical filter 26a will be referred to as "normal light", and the illumination light that passes through the second optical filter 26b will be referred to as "narrow-band light".

In this way, the filter turret 26 alternatingly extracts normal light using the first optical filter 26a and narrow-band light using the second optical filter 26b at a predetermined field rate while rotating. Note that the rotation position and rotation phase of the filter turret 26 are controlled by using a photo-interrupter 28 to detect an opening (not shown) formed in the vicinity of the outer periphery of the filter turret 26.

The light adjustment unit 22 has a variable diaphragm. The amount of illumination light from the filter turret 26 that enters the light adjustment unit 22 is adjusted by the opening degree of the variable diaphragm. The illumination light adjusted by the light adjustment unit 22 is condensed on one end surface of the light guide fiber bundle 13 by the condensing lens 23, and enters the light guide fiber bundle 13. The illumination light that entered the light guide fiber bundle 13 is guided to the distal end portion of the insertion tube 112. The illumination light guided to the distal end portion of the insertion tube 112 exits from the exit end of the light guide fiber bundle 13 and illuminates the subject in a body cavity. The illumination light that illuminates the subject is reflected by the subject and enters the imaging unit 10 as object light.

The imaging unit 10 includes an objective lens 10a and an image sensor 10b. The image sensor 10b is an interlace single CCD (Charge Coupled Device) image sensor, for example. The object light that enters the imaging unit 10 is received by the image sensor 10b via the objective lens 10a. The object light received by the image sensor 10b is converted into an image signal at a predetermined field rate and transmitted to the image processing unit 123 of the processor unit 120 via one of the wires 14. Note that for the sake of convenience in the description, the image signal for an EVEN field output by the image sensor 10b will be referred to as a "first image signal", and the image signal for an ODD field will be referred to as a "second image signal". Also, the timing of switching between normal light and narrow-band light by the filter turret 26 and the timing of switching of the imaging period (field period) in the image sensor 10b are synchronized with a field synchronization signal output by the image sensor driver 126. The EVEN field first image signal is an image signal generated by imaging a subject illuminated by normal light, and the ODD field second image signal is an image signal generated by imaging the subject illuminated by narrow-band light.

Also, the image sensor driver 126 transmits a field signal to the image processing unit 123 along with the first image signal and the second image signal. The field signal is a signal that indicates whether the first image signal or the second image signal was transmitted from the image sensor 10b to the image processing unit 123.

The image processing unit 123 includes a pre-process unit 40, a first memory 41, a second memory 42, an image compositing unit 43, a post-process unit 44, and an image evaluation processing unit 45.

The pre-process unit 40 performs signal processing such as AD conversion and gamma correction on the first image signal and the second image signal received from the image sensor 10b. Out of these image signals subjected to signal processing by the pre-process unit 40, the first image signal is transmitted to the first memory 41, and the second image signal is transmitted to the second memory 42.

The first memory 41 that operates as a first image signal storing means and the second memory 42 that operates as a second image signal storing means each successively store the received image signals. Note that there is a limit on the number of image signals (number of frames) that can be stored in the first memory 41 and the second memory 42. For this reason, if the first memory and the second memory receive a new image signal while the maximum number of image signals are stored, the new image signal is stored by overwriting the oldest image signal among the stored image signals.

Figure 5:
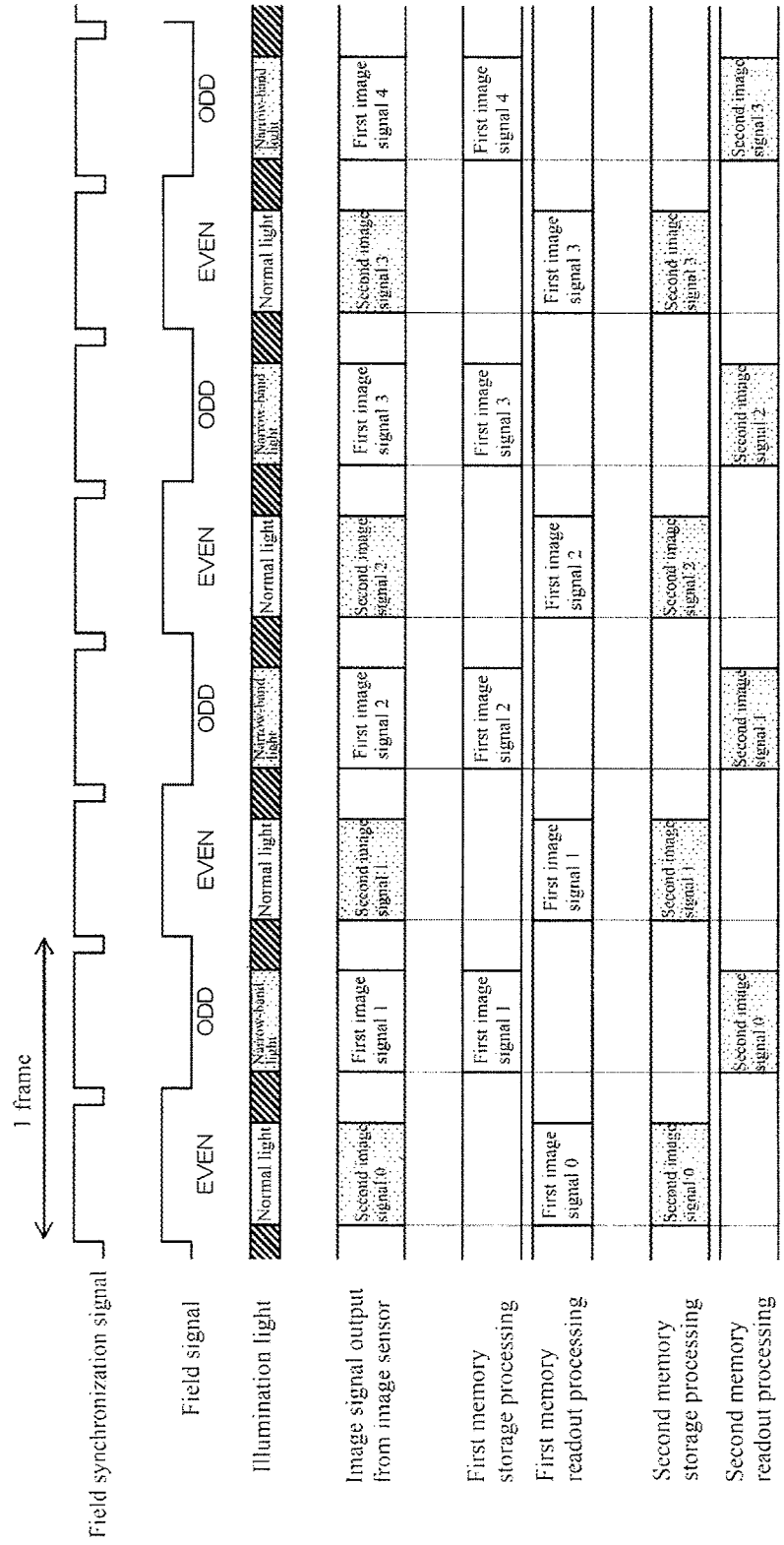
FIG. 5 is a diagram for describing change over time in a field synchronization signal, a field signal, and illumination light according to the embodiment of the present invention, as well as the timing at which image signals are output based on imaging signals, and the timing at which storage processing and readout processing are performed on image signals in memories.

FIG. 5 is a diagram showing change over time in the field synchronization signal, the field signal, and illumination light, as well as the timing at which image signals are output from the image sensor 10b, and the timing at which storage processing and readout processing are performed on image signals in the first memory 41 and the second memory 42. In FIG. 5, time progresses from left to right. The field synchronization signal is a two-value voltage signal that has a rectangular waveform, and the voltage thereof changes at a predetermined field rate ($\frac{1}{60}$ seconds in the present embodiment). The field signal is a two-value voltage signal that has a rectangular waveform. As shown in FIG. 5, the two values of "field signal" represent "EVEN" and "ODD". The timing at which the voltage of the field signal changes is synchronized with the rise of the voltage of the field synchronization signal. "Illumination light" shown in FIG. 5 denotes the type of illumination light that illuminates the subject. As shown in FIG. 5, when "field signal" is "EVEN", the subject is illuminated by normal light, and when "field signal" is "ODD", the subject is illuminated by narrow-band light.

First image signals of the subject illuminated by normal light are successively stored in the first memory 41 at the frame rate of the image sensor 10b ($\frac{1}{30}$ seconds in the present embodiment). Also, second image signals of the subject illuminated by narrow-band light are successively stored in the second memory 42 at the frame rate of the image sensor 10b. In FIG. 5, the successively stored first image signals and second image signals are denoted by different numbers. Note that processing time is required for the electrical signal processing performed by circuits of the processor unit 120 and the endoscope unit 110, such as signal processing in the pre-process unit 40 and writing processing for writing image signals to the first memory and the second memory. For this reason, deviation occurs between the timing of exposure by the image sensor 10b and the timing of output of the image signals (first image signal or second image signal). In FIG. 5, this deviation in timing is assumed to be equivalent to one field. For example, in FIG. 5, while the "ODD" field signal and the "first image signal 1" are output from the image sensor 10b, and the subject is being illuminated by narrow-band light, storage processing for storing the "first image signal 1" in the first memory 41 is performed, and readout processing for reading out the "second image signal 0", which was stored in the immediately previous field, from the second memory 42 is performed. Also, while the "EVEN" field signal and the "second image signal 1" are output from the image sensor 10b, and the subject is being illuminated by normal light, readout processing for reading out the "first image signal 1", which was stored in the immediately previous field, from the first memory 41 is performed, and storage processing for storing the "second image signal 2" in the second memory 42 is performed. Note that the deviation between the timing of exposure with the types of illumination lights by the image sensor 10b and the timing of output of image signals is not limited to being equivalent to exactly one field, and this deviation varies according to the processing time required in the circuits.

The image signals read out from the first memory 41 and the second memory 42 are transmitted to the image compositing unit 43. The image compositing unit 43 composites the first image signal and the second image signal of the same frame, and transmits the composited image signal to the post-process unit 44. The post-process unit 44 processes the composited image signal received from the image compositing unit 43, generates screen data for monitor display, and converts the generated screen data for monitor display into a predetermined video format signal. The converted video format signal is output to the monitor 130.

Figure 6:
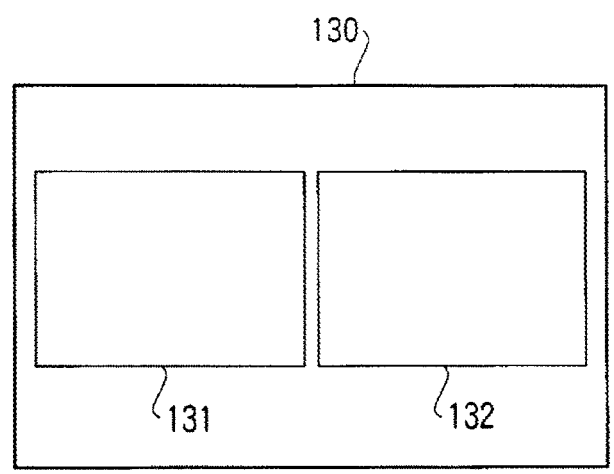
FIG. 6 is a diagram showing an example of a display screen of a monitor according to the embodiment of the present invention.

FIG. 6 shows an example of a display screen of the monitor 130. As shown in FIG. 6, an image 131 that is based on the first image signal (referred to hereinafter as a "normal light observation image") and an image 132 that is based on the second image signal (referred to hereinafter as a "narrow-band light observation image") are displayed side-by-side in the same screen on the monitor 130.

Next, moving image freeze processing of the present embodiment will be described.

If a freeze instruction is input to the input device 125 by the user (operator) of the endoscope system 100 while a moving image is being displayed on the monitor 130, the displayed moving image is paused (frozen) under control of the controller 124 that operates as an instruction receiving means. The frozen moving image is displayed as a still image on the monitor 130. A first image signal and a second image signal for display as a still image are selected by the image evaluation processing unit 45 from among the image signals of frames stored in the first memory 41 and the second memory 42. Hereinafter, for the sake of convenience in the description, the image signals selected by the image evaluation processing unit 45 will be referred to as "still image signals".

The image evaluation processing unit 45 operates as an image evaluation value calculating means. Specifically when image signals (first image signal and second image signal) of frames are stored in the memories (first memory 41 and second memory 42), the image evaluation processing unit 45 calculates image evaluation values for the stored image signals. Edge detection processing is used in image evaluation value calculation. Specifically, edge detection processing is count processing for counting the number of pixels that correspond to a clear (strong) edge.

The image evaluation processing unit 45 performs count processing on the first image signal of each frame stored in the first memory 41. In this count processing, for each frame, the number of pixel values in the first image signal that are greater than a predetermined threshold value is counted. The counted number of pixels becomes the image evaluation value of the first image signal. The higher the image evaluation value is, the less motion-blur or defocus there is in the normal light observation image.

The image evaluation value calculation performed on the first image signal is also performed by the image evaluation processing unit 45 on the second image signal of each frame stored in the second memory 42. The higher the image evaluation value of the second image signal is, the less motion-blur or defocus there is in the narrow-band light observation image.

The image evaluation processing unit 45 operates as an image signal selecting means. Specifically, when a freeze instruction is input to the input device 125, based on the calculated image evaluation values, the image evaluation processing unit 45 selects still image signals from among the image signals (first image signal and second image signal) stored in the memories (first memory 41 and second memory 42).

Next, consider the case where the image evaluation value is based on only motion-blur and defocus. In this case, there is a risk of a large time difference occurring between the time when the freeze instruction is input (referred to hereinafter as the "freeze timing") and the time when the image corresponding to the still image signal selected based on the image evaluation values was captured (referred to hereinafter as the "image capture timing"). When this time difference is larger, there are cases where a still image corresponding to the timing desired by the operator is not displayed on the monitor 130.

The still image displayed on the monitor 130 is more suitable the closer the capture timing is to the freeze timing. For this reason, the image evaluation processing unit 45 weights the image evaluation values according to the image capture timing. Specifically, the image evaluation processing unit 45 performs addition processing in which an addend is added to the image evaluation value or multiplication processing in which the image evaluation value is multiplied by a multiplier, and this addend or multiplier is higher the smaller the time difference is between the freeze timing and the image capture timing of the image signal. After the addition processing or the multiplication processing is performed on the image evaluation values of the image signals, the image evaluation processing unit 45 selects the image signal of the frame that has the highest image evaluation value (i.e., the still image signal) among the image signals of multiple frames. The processing performed by the image evaluation processing unit 45 for selecting the still image signal from first image signals of multiple frames and the processing performed by the image evaluation processing unit 45 for selecting the still image signal from second image signals of multiple frames are performed independently.

Accordingly, the first image signal and the second image signal that each have little motion-blur and defocus, and also have a small time difference between the freeze timing and the image capture timing, are independently selected as still image signals. The image compositing unit 43 and the post-process unit 44 operate as a displaying means. The still image signals are processed by the image compositing unit 43 and the post-process unit 44 and transmitted to the monitor 130, and thus a normal light observation image (still image) and a narrow-band light observation image (still image) are displayed side-by-side in the display screen of the monitor 130.

Here, the normal light and the narrow-band light have different wavelength bands and light intensities. When the wavelength bands and light intensities of illumination light are different, the conditions of the occurrence of motion-blur and defocus in an image change. For this reason, even in the same frame, the magnitudes of motion-blur and defocus are not necessarily the same between the normal light observation image and the narrow-band light observation image. However, according to the present embodiment, still image signal selection is performed separately for the first image signal and the second image signal. For this reason, even if the magnitudes of motion-blur and defocus are different between the first image signal and the second image signal, or the image capture timings (frames) that have little motion-blur and defocus are different, the image signal for an image that has little motion-blur and defocus is selected as the still image signal for both the first image signal and the second image signal.

An illustrative example of an embodiment of the present invention has been described above. The embodiments of the present invention are not limited to the embodiment described above, and various changes can be made within the scope of the technical idea of the present invention.

Although the image evaluation processing unit 45 performs image evaluation value calculation on both the first image signal and the second image signal in the present embodiment, the present invention is not limited to this. Image evaluation value calculation may be performed on only either the first image signal or the second image signal.

The following describes the case where the image evaluation processing unit 45 performs image evaluation value calculation on only the first image signal. The image evaluation processing unit 45 performs image evaluation value calculation processing on only the first image signal of each frame stored in the first memory 41. When a freeze instruction is input to the input device 125, the image evaluation processing unit 45 selects a still image signal from the first image signals of multiple frames based on the calculated image evaluation values. Next, the second image signal of the same frame as the selected first image signal is selected by the image evaluation processing unit 45 as the still image signal. Accordingly, it is possible to reduce the magnitudes of motion-blur and defocus in the normal light observation image, and also reduce the load of the image evaluation value calculation performed by the image evaluation processing unit 45. Note that the frame of the second image signal selected as the still image signal does not need to be the same frame as the selected first image signal. For example, the second image signal of the frame immediately before or after the frame of the selected first image signal may be selected as the still image signal.

Also, the image evaluation value may be calculated based on a difference value between the image signals of two consecutive frames. For example, in the case where a large amount of motion-blur occurs in an observation image due to a large amount of motion (fast motion) of the subject, the difference value between the image signals of two consecutive frames increases, and therefore a low image evaluation value is calculated. Also, in the case where a small amount of motion-blur occurs in an observation image due to a small amount of motion of the subject, the difference value between the image signals of two consecutive frames decreases, and therefore a high image evaluation value is calculated.

Also, although the example of interlace imaging is described in the present embodiment, progressive imaging may be substituted for interlace imaging in another embodiment.

The invention claimed is:

1. An endoscope system comprising:
a light source that alternatingly emits first illumination light and second illumination light at a predetermined cycle, the first illumination light and the second illumination light having different wavelength bands;
an imaging sensor that images a subject illuminated by the first illumination light and generates a first image signal, and that images the subject illuminated by the second illumination light and generates a second image signal;
a first memory that successively stores generated first image signals;
a second memory that successively stores generated second image signals;
a processor that performs operations including:
calculating first image evaluation values based on the stored first image signals;
calculating second image evaluation values based on the stored second image signals, independently of the first image evaluation values;
selecting a first display image signal from the stored first image signals, based on the calculated first image evaluation values; and
selecting a second display image signal from the stored second image signals, based on the calculated second image evaluation values, the second display image signal being selected independently of the first display image signal; and
a display that displays a first image that is based on the first display image signal and a second image that is based on the second display image signal at the same time;
wherein the first display image signal is selected independently of the second image signal evaluation values, and the second display image signal is selected independently of the first image signal evaluation values.

2. The endoscope system according to claim 1, wherein the processor further receives a freeze instruction from a user, and
wherein the processor weights each of the calculated first and second image evaluation values according to a time period between a time when an image corresponding to each of the first and second image evaluation values was captured and a time when the freeze instruction is received.

3. The endoscope system according to claim 2, wherein the processor performs the weighting by adding an addend to each of the first and second image evaluation values or multiplying each of the first and second image evaluation values by a multiplier, the addend or the multiplier increases, as the time difference decreases.

4. The endoscope system according to claim 1, wherein in a case where a new first image signal is generated by the imaging sensor when a predetermined number of first image signals are stored, the processor stores the new first image signal by overwriting a first image signal that has an oldest storage time among the stored first image signals, and
in a case where a new second image signal is generated by the imaging sensor when a predetermined number of second image signals are stored, the processor stores the new second image signal by overwriting a second image signal that has an oldest storage time among the stored second image signals.

5. The endoscope system according to claim 1, wherein the first illumination light is white illumination light and the second illumination light is narrow-band light, which includes light within a specific bandwidth narrower than the bandwidth of the white illumination light.

* * * * *